United States Patent
Hagedorn et al.

(10) Patent No.: US 10,344,274 B2
(45) Date of Patent: Jul. 9, 2019

(54) METHODS FOR SEPARATING NUCLEIC ACIDS WITH GRAPHENE COATED MAGNETIC BEADS

(71) Applicant: Life Magnetics, Inc., Ann Arbor, MI (US)

(72) Inventors: Kevin Hagedorn, Ann Arbor, MI (US); Saravana Murthy, Gaitersburg, MD (US)

(73) Assignee: Life Magnetics, Inc., Ann Arbor, MI (US)

( * ) Notice: Subject to any disclaimer, the term of this patent is extended or adjusted under 35 U.S.C. 154(b) by 0 days.

(21) Appl. No.: 15/888,702

(22) Filed: Feb. 5, 2018

(65) Prior Publication Data

US 2018/0155707 A1    Jun. 7, 2018

Related U.S. Application Data

(63) Continuation of application No. 15/858,140, filed on Dec. 29, 2017, now abandoned, which is a continuation-in-part of application No. 15/434,470, filed on Feb. 16, 2017, now abandoned.

(60) Provisional application No. 62/295,985, filed on Feb. 16, 2016.

(51) Int. Cl.
| | |
|---|---|
| *C12N 15/10* | (2006.01) |
| *C12Q 1/68* | (2018.01) |
| *C12Q 1/686* | (2018.01) |

(52) U.S. Cl.
CPC ......... *C12N 15/1013* (2013.01); *C12Q 1/686* (2013.01)

(58) Field of Classification Search
CPC .................... C12N 15/1013; C12Q 1/686
USPC ............................. 536/25.4; 435/6.1
See application file for complete search history.

(56) References Cited

U.S. PATENT DOCUMENTS

| | | | |
|---|---|---|---|
| 5,705,628 A * | 1/1998 | Hawkins ............ | C12N 15/1013 252/62.51 R |
| 5,898,071 A | 4/1999 | Hawkins | |
| 5,939,261 A | 8/1999 | Loewy et al. | |
| 6,342,387 B1 | 1/2002 | Hayashizaki et al. | |
| 6,355,792 B1 | 3/2002 | Michelsen et al. | |
| 6,787,307 B1 | 9/2004 | Bitner et al. | |
| 6,936,414 B2 | 8/2005 | Gundling | |
| 7,491,495 B2 | 2/2009 | Zielenski et al. | |
| 7,888,006 B2 | 2/2011 | Lenz | |
| 7,989,614 B2 | 8/2011 | Deggerdal et al. | |
| 8,017,332 B2 | 9/2011 | Liu | |
| 8,202,427 B2 | 6/2012 | Sauer et al. | |
| 8,222,397 B2 | 7/2012 | Bitner | |
| 8,247,545 B1 | 8/2012 | Colpan | |
| 8,513,405 B2 | 8/2013 | Jiang et al. | |
| 8,598,338 B2 | 12/2013 | Bair et al. | |
| 8,624,020 B2 | 1/2014 | Himmelreich et al. | |
| 8,729,252 B2 | 5/2014 | Himmelreich et al. | |
| 8,771,948 B2 * | 7/2014 | Wisniewski ....... | C12N 15/1006 435/6.11 |
| 8,801,936 B2 | 8/2014 | Grass et al. | |
| 9,206,469 B2 | 12/2015 | Forman et al. | |
| 9,322,024 B2 | 4/2016 | Gu et al. | |
| 9,708,645 B2 | 7/2017 | Ellis et al. | |
| 9,783,799 B2 | 10/2017 | Kim et al. | |
| 9,803,118 B2 | 10/2017 | Okamatsu | |
| 9,803,188 B2 | 10/2017 | Eshoo et al. | |
| 9,909,165 B2 | 3/2018 | Ellis et al. | |
| 2002/0110829 A1 | 8/2002 | Kolzau et al. | |
| 2004/0137449 A1 | 7/2004 | Nargessi | |
| 2005/0287583 A1 | 12/2005 | Smith et al. | |
| 2006/0147944 A1 | 7/2006 | Chomczynski | |
| 2009/0069554 A1 | 3/2009 | Finne | |
| 2010/0207051 A1 | 8/2010 | Fonnum et al. | |
| 2011/0224419 A1 | 9/2011 | Himmelreich et al. | |
| 2014/0291576 A1 | 10/2014 | Deggerdal et al. | |
| 2014/0363808 A1 * | 12/2014 | Gu ..................... | G01N 33/6893 435/5 |
| 2015/0232831 A1 | 8/2015 | Schlumpberger et al. | |
| 2015/0252357 A1 | 9/2015 | Bolle et al. | |
| 2016/0002622 A1 * | 1/2016 | Nelson ............... | C12N 15/1006 506/9 |
| 2016/0194684 A1 | 7/2016 | Lemonnier | |

(Continued)

FOREIGN PATENT DOCUMENTS

| | | |
|---|---|---|
| EP | 0796327 B1 | 7/2004 |
| EP | 1804045 A1 | 7/2007 |

(Continued)

OTHER PUBLICATIONS

Balcioglu et al. ACS Biomaterials Science & Engineering 2-15, 1, 27-36, (Year: 2015).*

(Continued)

*Primary Examiner* — Jezia Riley (74) *Attorney, Agent, or Firm* — Young Basile Hanlon & MacFarlane, P.C.

(57) ABSTRACT

Methods for separating and identifying nucleic acids utilize carbon coated magnetic beads. The method teaches that multivalent cations promote binding of single stranded nucleic acids to the beads and that the single stranded nucleic acids can be released with the addition of chelating agents that bind the multivalent cations such as EDTA. The method further teaches that fragile single stranded nucleic acids, such as RNA, can be stored on the surface of the beads. Lastly, the method also teaches that by iteratively adding complimentary DNA oligos, single stranded nucleic acids can be quantified or individually isolated using the carbon coated magnetic beads.

19 Claims, 10 Drawing Sheets

(56) References Cited

U.S. PATENT DOCUMENTS

| | | |
|---|---|---|
| 2017/0081656 A1 | 3/2017 | Karinaga et al. |
| 2017/0152509 A1 | 6/2017 | Ohashi |
| 2017/0211058 A1 | 7/2017 | Roth et al. |
| 2017/0253869 A1 | 9/2017 | Han et al. |
| 2017/0283791 A1 | 10/2017 | Fukushima et al. |
| 2017/0314010 A1 | 11/2017 | Hsieh et al. |
| 2017/0362586 A1 | 12/2017 | Hsieh et al. |

FOREIGN PATENT DOCUMENTS

| | | |
|---|---|---|
| EP | 1668127 B1 | 3/2010 |
| EP | 2163621 A1 | 3/2010 |
| EP | 2264184 A1 | 12/2010 |
| EP | 2295567 B1 | 11/2013 |
| EP | 2666778 B1 | 3/2016 |
| EP | 3222733 A1 | 9/2017 |
| EP | 2304028 B1 | 10/2017 |
| WO | 1991012079 A1 | 8/1991 |
| WO | 1996009379 A1 | 3/1996 |
| WO | 00/70040 A1 | 11/2000 |
| WO | 02/066993 A1 | 8/2002 |
| WO | 2004013155 A2 | 2/2004 |
| WO | 2006079660 A1 | 8/2006 |
| WO | 2008097342 A2 | 8/2008 |
| WO | 2010026167 A1 | 3/2010 |
| WO | 2011026028 A1 | 3/2011 |
| WO | 2011083429 A1 | 7/2011 |
| WO | 2012069660 A1 | 5/2012 |
| WO | 2015/120445 A1 | 8/2015 |

OTHER PUBLICATIONS

Huang Po-Jung Jimmy et al., "Separation of Short Single- and Double-Stranded DNA Based on Their Adsorption Kinetics Difference on Graphene Oxide", Nanomaterials (Basel), 2013, vol. 3, p. 221-228.

Park Joon Soo et al., "Desorption of single-stranded nucleic acids from graphene oxide by disruption of hydrogen bondings". Analyst, 2013, vol. 138, p. 1745-1749.

Balcioglu et al., "Smart-Polymer-Functionalized Graphene Nanodevices for Thermo-Switch-Controlled Biodetection", ACS Biomaterials Science & Engineering, 2015,1, pp. 27-36.

* cited by examiner

METHODS FOR SEPARATING NUCLEIC ACIDS WITH GRAPHENE COATED MAGNETIC BEADS

CROSS-REFERENCE TO RELATED APPLICATIONS

This application is a continuation of U.S. patent application Ser. No. 15/858,140, filed Dec. 29, 2017, which is a continuation-in-part of U.S. patent application Ser. No. 15/434,470, filed Feb. 16, 2017, which claims the benefit of U.S. Provisional Patent Application Ser. No. 62/295,985, filed Feb. 16, 2016, each of which is incorporated herein in its entirety by reference.

FIELD OF THE DISCLOSURE

This disclosure relates to nucleic acid purification and isolation, magnetic bead biological separations, and carbon and its allotropes

BACKGROUND

The need for effective techniques for isolating single stranded nucleic acid components from associated biological materials persists in a variety of research and development endeavors. Heretofore, nucleic acid separation techniques can include various chelating agents, solid support columns using fibrous or silica matrices to bind nucleic acids and/or magnetic beads to which nucleic acid can bind. The isolation methods presently in use do not provide effective yield in all instances. Thus, it would be desirable to provide a method and material that can provide more effective and efficient nucleic acid isolation.

SUMMARY

An improved method for separating single stranded nucleic acids from a sample that includes the steps of: providing a mixture containing nucleic acids; and providing carbon coated material; providing a chaotropic salt such as guanidinium thiocyanate; providing alcohols such as ethanol or organic solvents; and creating a complex of the carbon coated material and nucleic acids. In certain embodiments, the carbon-coated material employed can be in the form of magnetic beads, silica gel or various polymeric materials. The method disclosed herein can also include the steps of removing the carbon coated material complexed with nucleic acids from the resulting mixture by means of magnetic separation or centrifugation. The method may further include the steps of washing the carbon-coated material and nucleic acids complex with alcohol based solutions. The method may also include the step of reversing the complexation of the nucleic acids with the carbon-coated material by the addition of water or aqueous liquids.

In certain embodiments, carbon coated magnetic beads may be employed that can have a magnetic core coated surrounded by a suitable carbon material. In other embodiments, the carbon coated material may have a non-magnetic core such as silica coated with a suitable carbon material.

BRIEF DESCRIPTION OF THE DRAWINGS

The various features, advantages and other uses of the present apparatus will become more apparent by referring to the following detailed drawings.

DETAILED DESCRIPTION

An improved method of separating single stranded nucleic acids from a mixture is disclosed herein. The method includes the steps of providing a sample containing single stranded nucleic acids and contacting the sample containing single-stranded nucleic acid with a carbon-coated material, at least one chaotropic salt, and at least one alcohol to effect separation.

Figure 1:
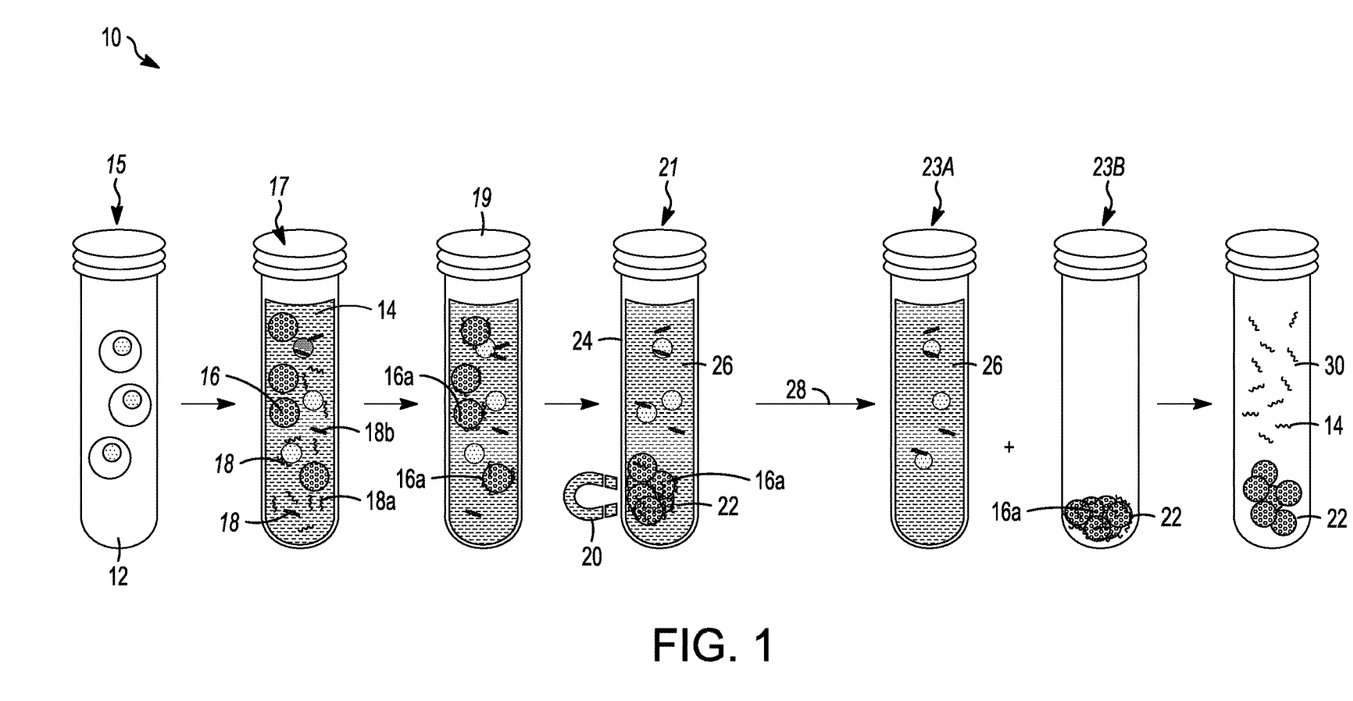
FIG. 1 is a schematic drawing for how single stranded nucleic acids are isolated.
Figure 2:
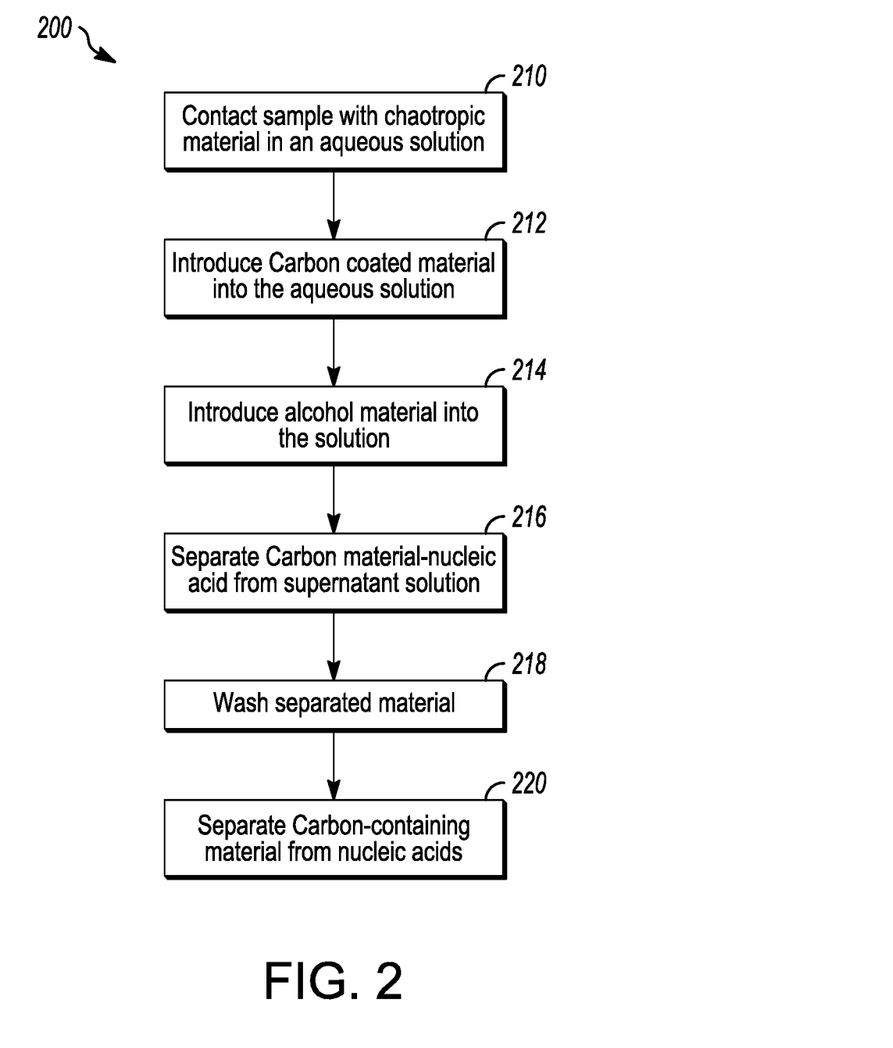
FIG. 2 is a flow chart of an embodiment of the process disclosed herein and depicted in FIG. 1.

An embodiment of the separation process as disclosed herein is illustrated in FIG. 1 and described as a flow chart in FIG. 2.

As depicted FIG. 1, the process 100 begins with a collected sample 12 containing nucleic acids and a suitable solvent, such as would be found in in various microorganisms, plant and animal specimens such as mammalian tissue, a non-limiting example of which is human liver tissue. The collected sample 12 can be maintained in a suitable vessel such as that depicted in FIG. 1 at reference numeral 15. The process as disclosed herein can take placed in a suitable reaction vessel or container or semi-permeable matrix. In the embodiment depicted in FIG. 1, the reaction vessel is an elongated tube.

To this sample 12 is added a chaotropic material 14 such as a chaotropic salt solution and carbon-coated materials 16. This creates a mixture of nucleic acids, chaotropic materials 14, and carbon-coated materials 16 as at reference numeral 17. Without being bound to any theory, it is believed that contact between the nucleic acids present in the sample and the chaotropic material results in separation of single stranded nucleic acid material 18*a* and double stranded nucleic acid material 18*b* into the solution with single and double stranded nucleic acid material collectively referend to as reference numeral 18.

To this resulting mixture is added an alcohol as at reference numeral 19. The alcohol of choice can be a short-chain alcohol such as ethanol or the like. Once the nucleic acid material 18, chaotropic material 14, carbon-coated material 16, and solvent are present together, the single-stranded nucleic acids 18a present in the sample complex with the carbon-coated material 16 and create a nucleic acids-carbon complex 16A as at reference numeral 19.

While the embodiment depicted in FIG. 1, depicts a process in which the various material components are introduced in a specific sequential order, it is considered within the purview of this disclosure that the four materials may be provided in any order such that the four materials are present together before the separation step such as that denoted at reference numeral 21. Where desired or required, the four components can be admixed to ensure contact between the various components.

Once all four material components are in admixture together, the admixed materials can remain in contact with one another for a suitable period sufficient for the nucleic acids present in the initial sample to complex with the carbon coated material. Where desired or required, the contact interval can be between 1 second and 5 minutes. In certain embodiments, the complexing period can be between 10 seconds and 5 minutes.

The carbon-coated material can be configured in any suitable size and shape that would facilitate complexing with the desired nucleic acids. Non-limiting examples of such configurations include beads in which each individual bead has an interior core and an outer surface, the beads composed of one of the following: a magnetic metal containing at between 20 and 40% by weight of a metal selected from the group consisting of Ni, Fe, Co, or mixtures thereof, silica or polymeric substrates, and wherein the carbon coating is present as a carbon layer on at least a portion of the outer surface of the bead, the carbon layer comprising at least one of graphene, pyrolytic carbon or a mixture of graphene and pyrolytic carbon, and wherein the multivalent cations are alkali earth metals or alkali earth metal salts or mixtures thereof. Thus, in certain embodiments, it is contemplated that magnetic particles can be used as the carbon-coated material 16. In situations where carbon coated materials have a magnetic substrate, it is contemplated that exposure to a suitable magnetic field such as that produced by magnet 20 will produce separation between the nucleic acid carbon material complexes 16A and the liquid components present resulting in the development of a supernatant solution 26 and collected nucleic acids complexed with carbon material 16A. This may be accomplished by placing a magnet 20 near a specific location on the exterior of the reaction vessel or container as at reference numeral 22 to collect the carbon coated material and facilitate the process of separation as at reference numeral 28 and illustrated in FIG. 1. This results in a supernatant solution 26 that comprises double stranded nucleic acid, as well as other materials that may be present in the initial sample as depicted in reference numeral 23A. The complexes 16A can be transferred to a separate vessel for additional processing as at reference numeral 23B.

Where desired or required, the complexed carbon material 16A can be washed one or more times to ensure that all the supernatant liquid containing the cellular contaminants is removed. The washing step may be performed by contacting the separated material with one or more portions of a solution containing one or more of alcohols. The washing step may be performed multiple times to ensure that all the cellular contaminants present in the original supernatant have been removed. After several washes with a material such as an ethanol solution, the wash step can be completed by removing all of the wash solution. Air drying or other drying means may be employed to speed removal of the alcohol solution from the complex of the carbon coated material and nucleic acids. Pure water or water with less than 1M salt can then be added at reference numeral 30 in order to facilitate removal of the nucleic acids from complex with the carbon-containing material. In certain embodiments, it is contemplated that 50 µl or 100 µl of pure water can be employed in situations in which around 1 to 5 million cells are used as the source sample, yielding a solution with about 10 to 100 µl g of single stranded nucleic acid (RNA) dissolved in the pure water solution.

An embodiment of the separation process is illustrated in the flow chart in FIG. 2 in which nucleic acids are separated from a mixture using a chaotropic material such as a chaotropic salt solution, a polar solvent such as ethanol, and a carbon coated material.

As depicted in FIG. 2 at reference numeral 200, a sample containing nucleic acids is contacted with a chaotropic material such as a chaotropic salt to form an aqueous solution as at reference numeral 210. Carbon-coated materials are introduced to the aqueous solution at reference numeral 212. Alcohols are introduced to the aqueous solution at reference numeral 214. It is also considered to be within the purview of this disclosure that the four materials may be provided in any order such that the four materials are present together prior to any separation operations on the resulting solution. The process as disclosed herein can occur in a suitable reaction vessel or container.

Once all four material components are in mixture together, the materials can remain in contact with one another for a suitable period sufficient for the nucleic acids present in the initial sample to complex with the carbon coated material such as carbon beads. Where desired or required, the contact interval can be between 1 s and 5 min.

Once formed, the complexes of nucleic acids and carbon-containing material are separated from the supernatant liquid as at reference numeral 616. The resulting supernatant liquid can contain the initial liquid components in addition to extraneous cellular component material.

In certain embodiments, it is contemplated that magnetic beads coated with carbon can be used as the carbon-coated material. Separation can be accomplished by one or more mechanisms including, but not limited to, decanting, filtration and various mechanical separation methods. In situations where carbon coated beads had a magnetic substrate, it is contemplated that the separation step utilizing magnetic beads can be accomplished by placing a magnet near the exterior of reaction vessel or container to collect the carbon coated material and facilitate removal of the remaining solution. If the substrate onto which the carbon is coated is not magnetic, physical removal, centrifugation, or other methods may be used to separate the carbon material.

Where desired or required, the complexed carbon material can be washed one or more times to ensure that all the supernatant liquid containing the cellular contaminants is removed as at reference numeral 218. The washing step may be performed by contacting the separated material with one or more portions of a solution containing one or more of alcohols enumerated previously. The washing step may be performed multiple times to ensure that all the cellular contaminants present in the original supernatant have been removed. After several washes with a material such as an ethanol solution, the wash step can be completed by removing all of the wash solution. Air drying or other drying means may be employed to speed removal of the alcohol solution from the complex of the carbon coated material and nucleic acids. Purified water or water with less than 1M salt can then be added in order to facilitate removal of the nucleic acids from complex with the carbon-containing material at reference numeral 220. In certain embodiments, it is contemplated that, 50 µl or 100 µl of this water can be employed to release the single stranded nucleic acids.

Figure 3:
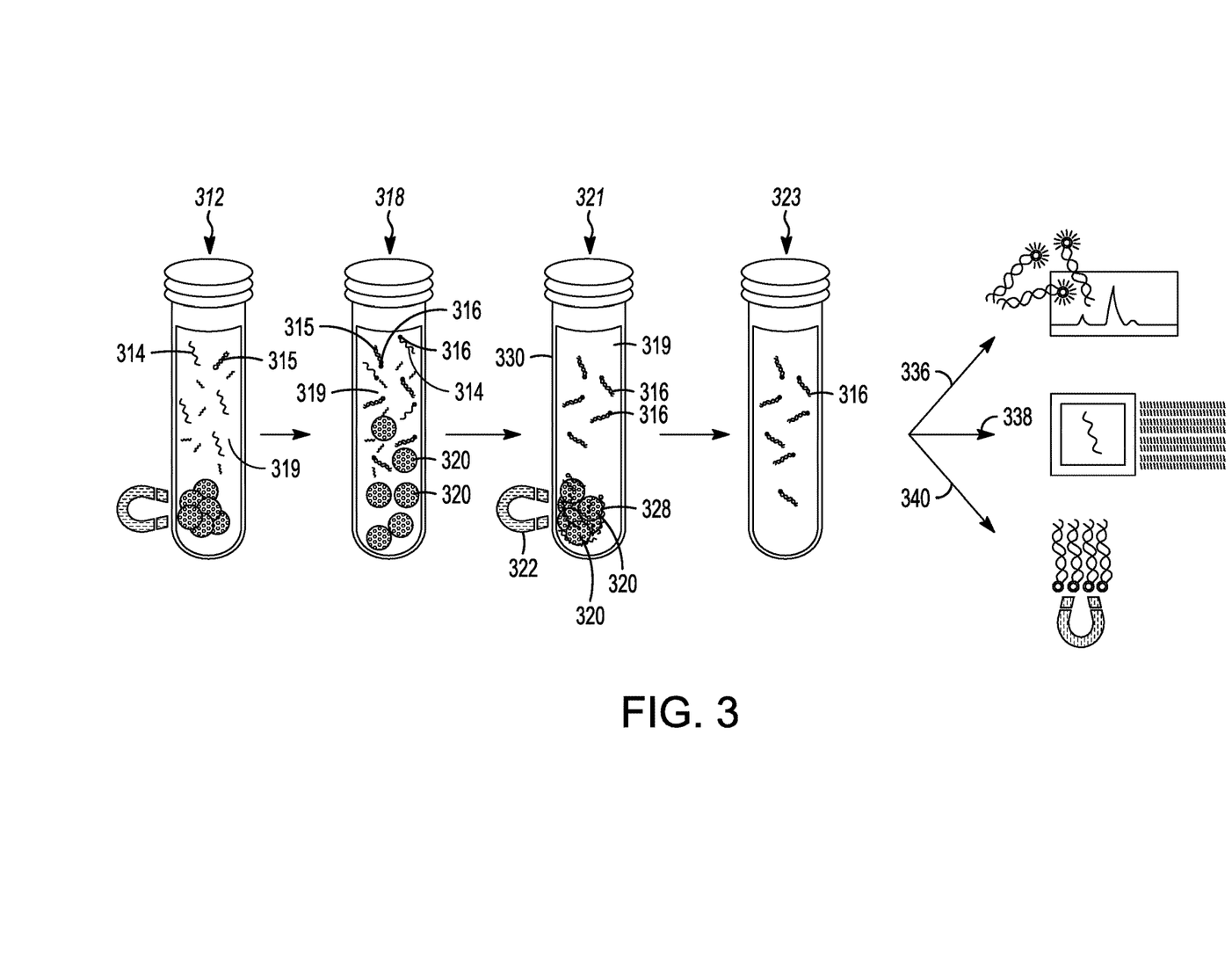
FIG. 3 is a schematic drawing for how a single stranded nucleic acid in a sample may be isolated and may also be quantified.
Figure 4:
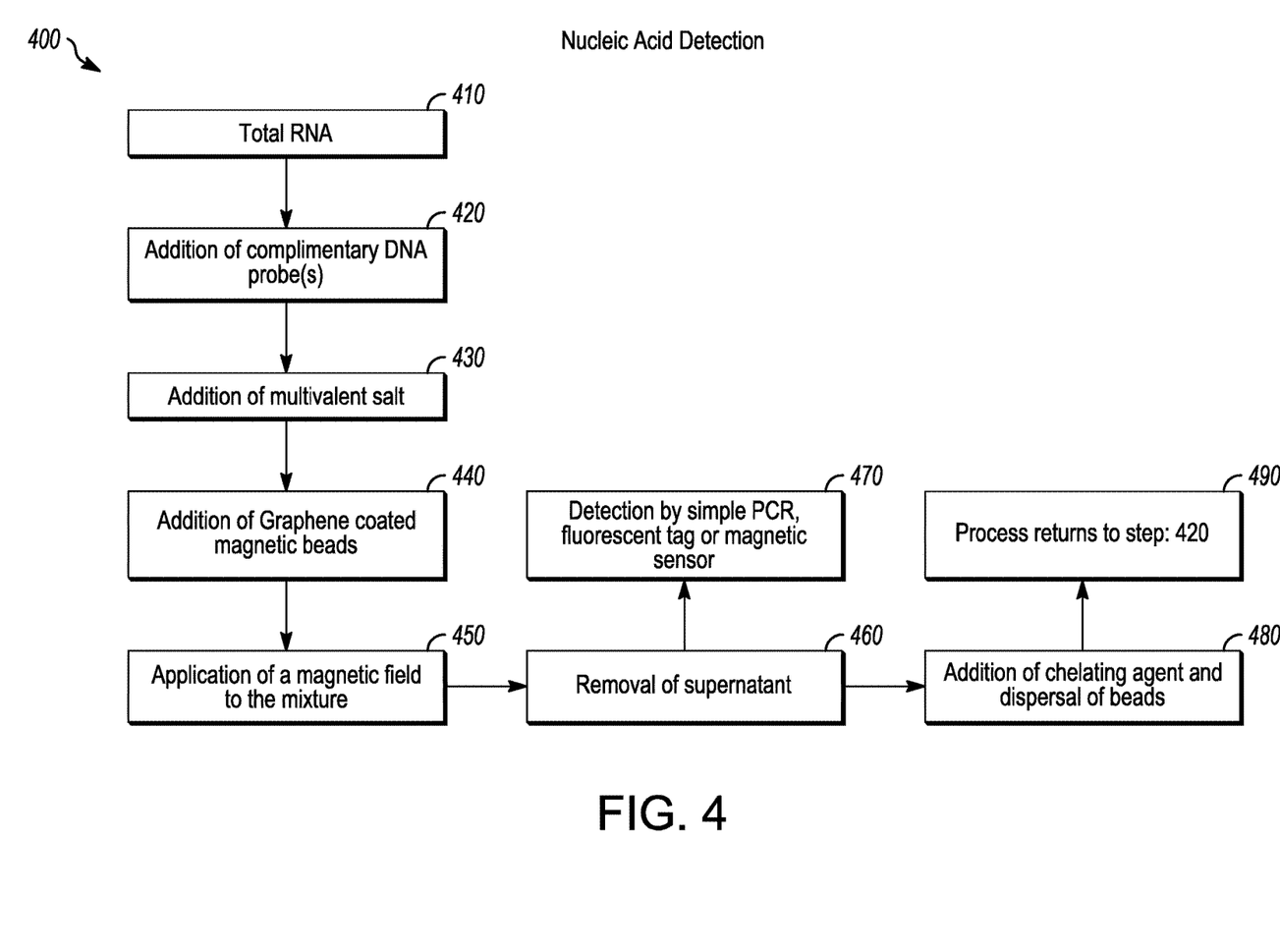
FIG. 4 is a flow chart for the process of how a single stranded nucleic acid in a sample may be isolated and may also be quantified.

The method as disclosed herein can also be employed to isolate and quantify a single stranded nucleic acid material with specific sequencing. A non-limiting exemplary method is illustrated in FIG. 3. A biological material to be analyzed is collected as at reference numeral 312, which may be the result of process 100. The sample in question can contain target single stranded nucleic acids 314 as well as double stranded nucleic acids 315 some of which are nucleic acids that contain a desired sequence for quantification together in a suitable solution 319.

Specific probes 316 can be added to the sample as illustrated at reference numeral 318 and allowed to react with any complementary nucleic acid material that is present in the sample 314 to form a duplex comprising the probe and the target. At step 317, a chaotropic salt, a suitable carbon-coated material 320, and an organic solvent are added to the solution if not already present. Once all four material components are in admixture together, the materials can remain in contact with one another for a suitable period sufficient for the single stranded nucleic acids 314 present in the initial sample to complex with the carbon coated material 320. Where desired or required, the contact interval can be between 1 second and 10 minutes, with intervals between 10 seconds and 5 minutes being employed in certain embodiment. The duplexes which contain both a probe 316 and a double stranded nucleic acid 315 target remain in solution 319.

In situations where carbon coated beads 320 have a magnetic substrate, it is contemplated that separation of the supernatant containing the duplex double stranded nucleic acids 315 and single stranded nucleic acids 314 complexed with carbon material 320 may be accomplished by placing a magnet 322 near the exterior of reaction vessel or container 324 to collect the carbon coated material as a pellet and facilitate the process of separation.

It is contemplated that the complementary nucleic acid material may be modified with a protein which may be used to isolate strands with specific sequencing. Once separated the duplex double stranded nucleic acids 315 modified with complementary proteins to those on the complementary nucleic acids may be added to the mixture to concentrate or isolate the target sequences. By way of non-limiting example, biotin may be attached to the complementary nucleic acids and streptavidin may be attached to a substrate or magnetic beads.

Separation of the supernatant liquid from contact with the carbon coated beads 320 yields a solution of the duplex material 316 that is amenable to various analytic techniques including, but not limited to florescent tag detection 336, simple PCR 338, magnetic sensor detection 340 and the like.

Figure 10:
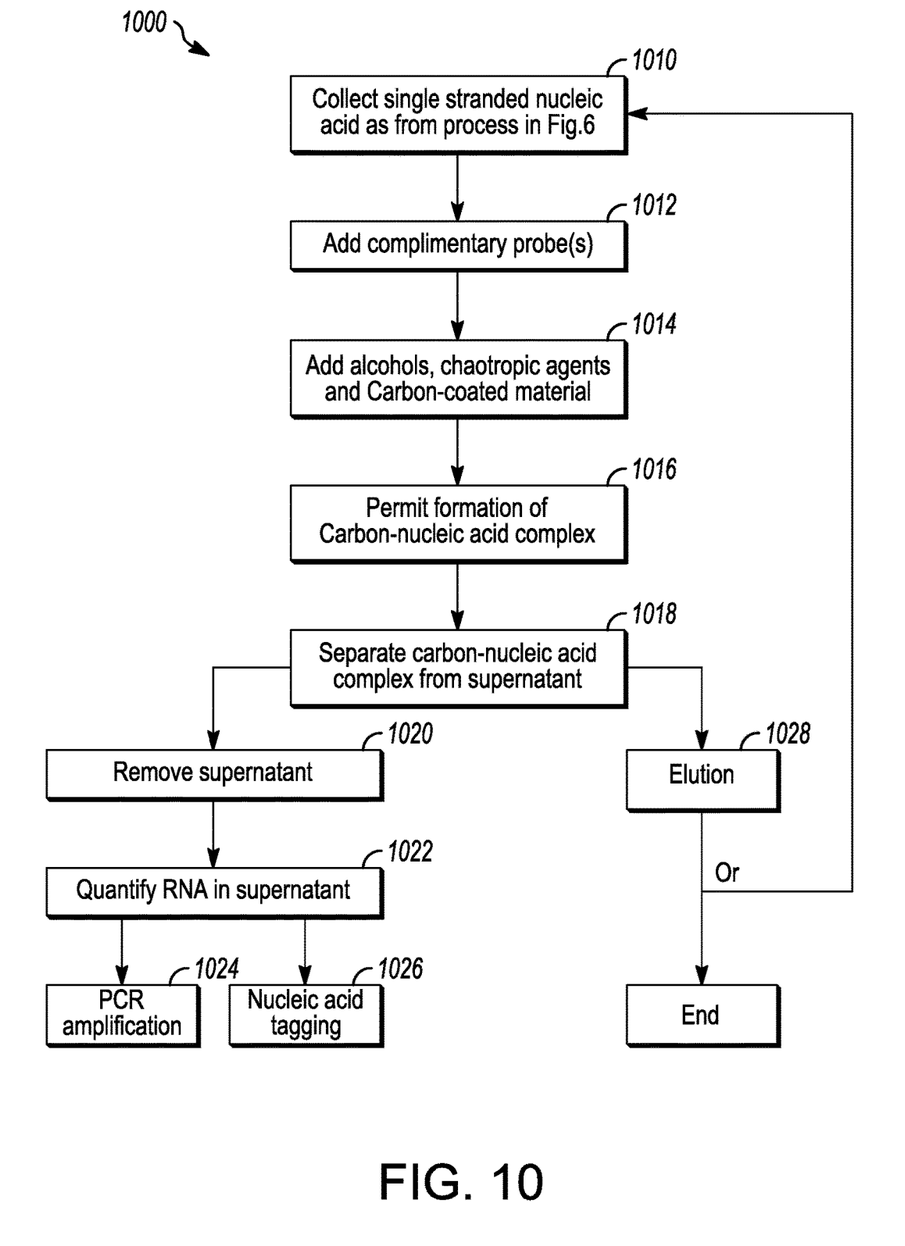
FIG. 10 is a flow chart for the process of how sequence specific analysis may be performed using chaotropic salts, alcohols, and carbon coated materials.

It is further conceived that the method as disclosed herein can be employed to perform sequence specific analysis and one non-limiting example of such a procedure is further illustrated in the flow chart diagram of FIG. 10 as at reference numeral 1000. A suitable sample of single stranded nucleic acids can be collected as at reference numeral 1010. It is contemplated that the single stranded nucleic acid can be derived from any suitable source or by any suitable method; one suitable process for separating and producing single stranded nucleic acid process disclosed herein in FIG. 6.

In the process as disclosed, at least one complimentary nucleic acid probe can be added to the collected material as at reference numeral 1012. It is contemplated that the nucleic acid probe can be a suitable diagnostic material. Non-limiting examples of such material include DNA, RNA, as well as synthetic nucleic acids such as peptide nucleic acids. If desired or required, the added material can be allowed to react with the single strand nucleic acid for a suitable interval.

Once any optional reaction interval has elapsed, alcohols, chaotropic materials such as chaotropic salts, and a carbon coated material such as those described herein can be added to the sample to initiate binding of the single stranded nucleic acids to the carbon-coated material as at reference numeral 1014. In certain embodiments, it is contemplated that this step will resemble the process step outlined in with regard to FIG. 6. It is also considered with in the purview of this disclosure that where little or no protein or cellular contamination is present, the addition of chaotropic materials such as chaotropic salts may be reduced or eliminated entirely, It is contemplated that the complex of the carbon coated material and single stranded nucleic acids that is produced may also contains complimentary probes which were added at reference numeral 1012 but do not find a target with which to hybridize.

Where desired or required, the resulting material can be permitted to form suitable complexes of the single stranded nucleic acid to which complementary probes have bonded and carbon-containing material as at reference numeral 1016. The formation interval can be any suitable period between 10 seconds and 24 hours in certain embodiments.

The resulting complex of nucleic acid and carbon coated material can then be separated as at reference number 1018. Separation can be accomplished by one or more mechanisms including, but not limited to, decanting, filtration and various mechanical separation methods. In situations where carbon coated beads have a magnetic substrate, it is contemplated that the separation step utilizing magnetic beads can be accomplished by placing a magnet near the exterior of reaction vessel or container or semi-permeable matrix to collect the carbon coated material and facilitate removal of the remaining solution.

The resulting supernatant can be removed for further analysis as desired or required as at reference numeral 1020 contains double stranded hybrids of the target and complimentary nucleic acids, which may be quantified as at reference numeral 1022. Non-limiting examples of suitable quantification methods include by PCR amplification reference numeral 1024, or by labeling the synthetic nucleic acid with a detectable fluorescent or magnetic tag as at reference numeral 1026. It is within the purview of this disclosure that the synthetic nucleic acids may be labeled before being added to the sample as at reference numeral 1012. It is also contemplated that the probes can be labeled after the supernatant is separated from the nucleic acid -carbon complex as at reference numeral 1026.

The nucleic acids that are complexed with the carbon material may be washed and eluted from the carbon coated material as at reference numeral 1028. Where desired or required, the complexed carbon material can be washed one or more times to ensure that all the supernatant liquid containing the cellular contaminants is removed as at reference numeral. The washing step may be performed by contacting the separated material with one or more portions of a solution containing one or more of alcohols enumerated previously. The washing step may be performed multiple times to ensure that all the cellular contaminants present in the original supernatant have been removed. After several washes with a material such as an ethanol solution, the wash step can be completed is completed by removing all of the wash solution. Air drying or other drying means may be employed to speed removal of the alcohol solution from the complex of the carbon coated material and nucleic acids. Pure water or water with less than 1M salt can then be added in order to facilitate removal of the nucleic acids from complex with the carbon-containing material. In certain embodiments, it is contemplated that, in certain embodiments, 50 µl or 100 µl of pure water can be employed in situations in which around 1 million cells are used as the source sample. The resulting sample of single stranded nucleic acids eluted as at reference numeral 1028 is suitable for use as a sample at 1010 and the process may be repeated.

The carbon-coated material can be composed of a suitable substrate having an outer surface with a suitable carbon material covering at least a portion of the outer surface of the substrate. The resulting carbon-nucleic acid complex may be separated from the remaining materials by various separation techniques. The techniques employed can be chosen based on factors such as the nature of the of the substrate material employed.

As used herein the term "nucleic acid probe" or "antibody probe" refers to a chain of nucleic acids selected so that it contains bases that are complementary or have affinity with corresponding positions in at least one section of the length of the nucleic acid chain under study. The complimentary nucleic acid probe may be longer than the target and have additional bases with an arbitrary sequence. Anti-nucleic acid antibody may have additional chemical modifications such as biotin tag. The complimentary probe may be synthetic nucleic acids such as peptide nucleic acid (PNA) or Morpholino and locked nucleic acid (LNA) or glycol nucleic acid (GNA) or threose nucleic acid (TNA).

Also disclosed is a composition that comprises a carbon coated substrate and single-stranded nucleic acid complexed therewith.

The carbon coated material as disclosed herein is one that will complex with single stranded nucleic acid material present in a sample. The single stranded nucleic acid material can include various naturally derived and/or synthetically prepared nucleic acids such as RNA, including any added complimentary nucleic acid probes if the target for these probes is not present in the sample under study. Particles with the single-stranded nucleic acids bound to the magnetic beads may be removed by application of a magnetic field, centrifugation, precipitation and the like.

In certain embodiments, the carbon coated material will include a substrate that is configured as a particulate material such as beads, or other spheroid bodies. When the substrate is configured as beads or other particulate geometries that are nanoparticulate in size; having a diameter between 20 and 200 nm or between 10 nm and 100,000 nm in certain embodiments.

Figure 5:
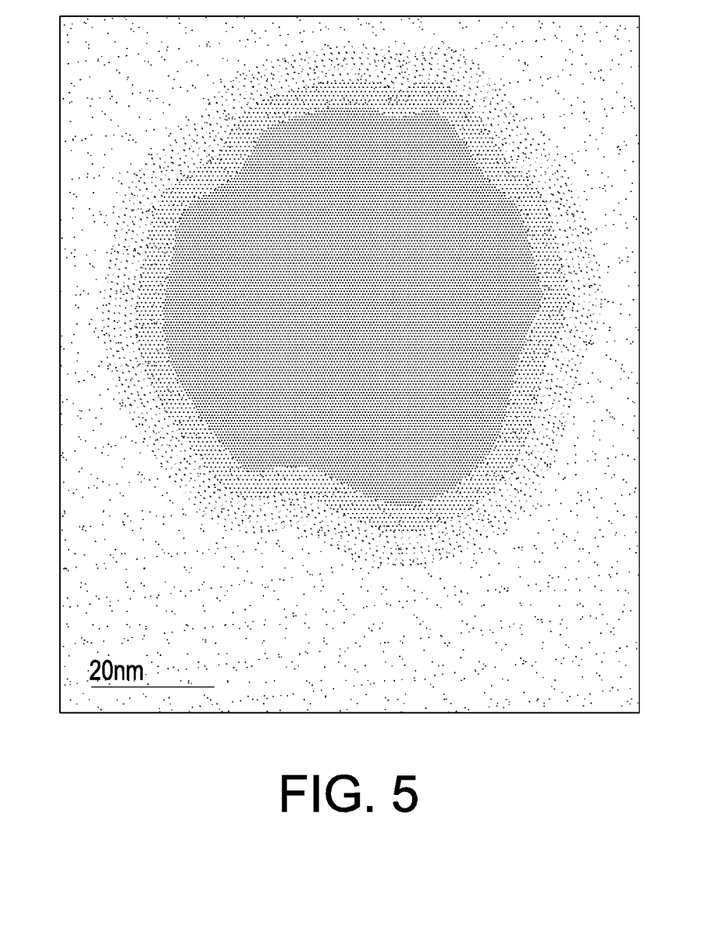
FIG. 5 is a transmission electron micrographs of a carbon coated magnetic beads which may be used in this process.

In certain embodiments, the carbon material can include one of more of the following: pyrolytic carbon, graphite, graphene. In certain embodiments, the suitable material is a material with a metal core that is surrounded by a carbon coating in which the carbon creates a generally seamless conformal coating. A suitable carbon coated material that can be used in the process as disclosed herein can be one such as the bead configuration presented in FIG. 5. Referring to FIG. 5, there is depicted a transmission electron micrograph in which a metal core composed of $Fe_{65}Co_{35}$ is surrounded by a carbon coating. This carbon coating has multiple layers, in which each layer is similar to graphene and there may be coupling between the layers. The presented carbon coated material structure is particularly well suited to the described process because the carbon creates a conformal coating without a seam around the metal core. Exposure of the metal core to water has undesirable effects due to oxidation of the metal. Oxidation of the metal may lead to undesirable properties such as binding DNA and reduction of magnetic moment. Suitable magnetic material that can be employed as the substrate is available commercially from Metastable Materials, Inc., doing business as Life Magnetics.

Carbon coated magnetic materials may be prepared by the laser manufacturing process disclosed in WO2015095398A1 which is disclosed herein by reference. It is contemplated that carbon coated materials can be prepared by positioning a laser is incident on target in a solvent such that the pulsed laser produces laser pulses having a pulse duration greater than 1 ps at a wavelength between 200 nm and 1500 nm at a pulse repetition rate of at least 10 Hz and a fluence greater than 10 $J/cm^2$. The laser beam may be scanned across the surface of the target; i.e., the desired core material (Silica, magnetic metal and the like). Non-limiting examples of satiable magnetic metal material includes metals and alloys containing iron, nickel, cobalt, or the like as well as mixtures and alloys of the aforementioned. The solvent employed can be an organic solvent which contains carbon and in certain embodiments will be composed of xylenes, toluene, benzene, or mixtures thereof. Where desired or required, the organic solvent may further include any hydrocarbon containing benzene rings. In certain embodiments, the magnetic beads employed will have a saturation magnetization between 10 and 80 A $m^2$/kg (emu/g); a coercive force between 0.8 and 15.9 KA/m, and a sedimentation rate between 2% and 15% in 30 minutes.

It is envisioned that the chaotropic material imparted may be may be provided independently in certain embodiments or may be introduced in combination with various other components depending on the nature of the sample containing the single-stranded nucleic acids. In certain embodiments, the chaotropic material composition may further contain components on or more additional components. These include, but are not limited to one or more of the following: ethylenediaminetetraacetic acid (EDTA), dithiothreitol (DTT), 2-mercaptoethanol (BME), Lithium Chloride (LiCl), Urea, N-lauroylsarcosine, IGEPAL 630, NP-40, SDS (sodium dodecyl sulfate), TCEP (tris(2-carboxyethyl) phosphine), Tributylphosphine (in N-methyl-2-pyrrolidinone), glycogen or the like. Where desired or required this compound can be present t a concentration of between 0.001% and 1% by volume. Without being bound to any theory, it is believed that the compound functions to inhibit protein activity. The chaotropic composition can also include a suitable buffer compound present at a concentration suitable to impart buffering characteristics to the composition.

Non-limiting examples of suitable buffer compounds include tris(hydroxymethyl)aminomethane (Tris), citric acid, sodium citrate, (3-(N-morpholino) propanesulfonic acid) (MOPS), 2-(N-morpholino)ethanesufonic acid (MES) as well as mixtures of these compounds. In certain embodiments, the buffer compound(s) may be present at a concentration between 50 mM and 500 mM to buffer the pH of the solution. The composition can also include detergents such as Triton X-100, or sodium dodecyl sulfate (SDS) or Tween- 20 or Tween-40 or N-lauroylsarcosine or IGEPAL 630 orNP-40 where desired or required.

In one non-limiting example of a suitable chaotropic material that can be employed one or more embodiments of the method as disclosed herein may be a solution of chaotropic salts which also contains between 1 to 100 mM EDTA, 1 to 100 mM of a buffer composed of citric acid, sodium citrate, and/or Tris, 0.01 to 5 volume % Triton X-100, and 0.1 to 5 mM DTT. The pH of the solution may be between 3 to 10. In one exemplary case, the chaotropic material is a chaotropic salt solution of 4M guanidinium thiocyanate, 20 mM citric acid buffer, and the pH is adjusted to 5.

It is further envisioned that, in certain embodiments, additional wash steps may be necessary as would be the case for biological substances having a high protein content such as blood. The process as disclosed herein may include one or more additional washing steps in which the wash solution employed may contain suitable materials employed individually or in combination such as reducing agents, ethanol, and chaotropic salts such as guanidinium thiocyanate, to aid in the solubilization and removal of the protein. For example, an additional wash step may be included which uses a wash solution composed of 0.6M to 2M chaotropic salts such as guanidinium thiocyanate, and 30% to 60% alcohol by volume. If this additional wash step is included, it is contemplated that a final washing step with a solution of ethanol without chaotropic salts will still occur.

It is envisioned that the chaotropic material may be chaotropic salts solutions other than guanidinium thiocyanate, such as guanidinium chloride, guanidinium bromide, guanidinium fluoride, guanidine acetate, guanidine sulfate, guanidine nitrate, guanidine carbonate, or may be other chaotropic compounds such as guanidine hydrochloride, urea, thiourea, lithium acetate, or lithium perchlorate and these compounds may have different efficacy in the process, it is expected different concentration ranges may be required depending on the efficacy of the salt. The chaotropic material guanidinium thiocyanate is used as a salt solution such that the concentration of the guanidinium thiocyanate salt is 0.1 to 1 M when the four materials are present together at reference numeral 21. These other compounds may be expected to have similar effects but at different concentrations, meaning that the concentration of chaotropic salts may be 0.01M to 4M at reference numeral 21 depending on the identity of the chaotropic salt, which other components are present, and the pH of the solution.

Figure 6:
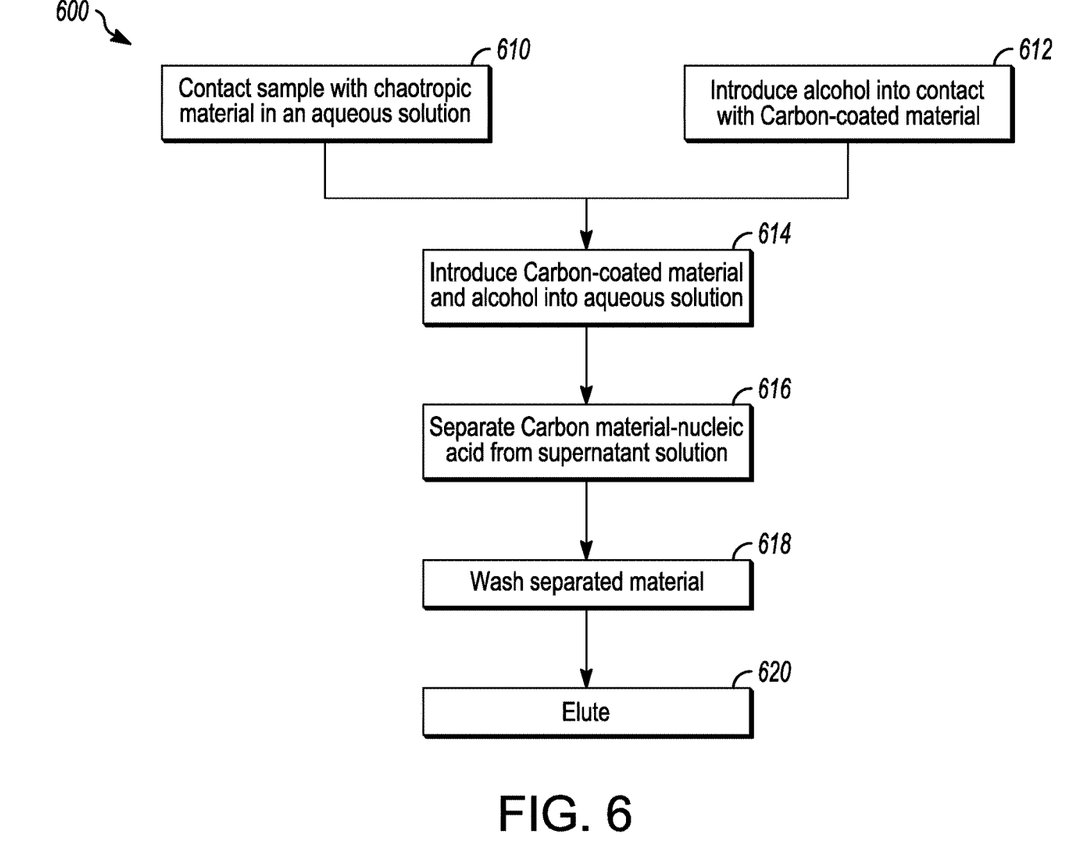
FIG. 6 is a flow chart for the process of separating and producing a single stranded nucleic acid process.

In the process as disclosed, a short chain alcohol such as ethanol can be added to the composition in an amount sufficient to facilitate complexation of single stranded nucleic acids with carbon materials such as carbon-coated magnetic beads. In certain embodiments, the short-chain alcohol can be added such that the final concentration of the chaotropic material such as guanidinium thiocyanate is between 0.1 M and 1M and the short-chain alcohol composes between 40 vol % and 80 vol % of the resulting solution employed at reference numeral 21 or reference numeral 615 in the flow chart. It has been found that under these conditions, single stranded nucleic acids complex with the carbon coated magnetic beads selectively rather than complexing with double stranded nucleic acids. It is also conceived that alcohols other than ethanol may be used, and depending on the alcohol, the ideal percentage of the total volume may be different. Alcohols such as propanol, methanol, butanol, phenol, and the like may replace ethanol. It is further conceived that a range of 20 vol % to 90 vol % alcohols may be used.

In certain embodiments, it is contemplated that the mixture which contains the sample containing nucleic acids, the carbon-coated material, the chaotropic material, and the alcohols, has carbon-coated beads at a concentration between $1 \times 10^5$ nanoparticulate beads per ml and $1 \times 10^{20}$ nanoparticulate beads per ml.

It is contemplated that the process and material as disclosed herein can be employed is to store RNA long term. RNA is known to be fragile and to degrade upon exposure to various enzymes and proteins extant in the environment. One non-limiting example of such material is ribonuclease (RNase). It has been found that single-strand nucleic acids such as RNA bind to the surface of the carbon-coated magnetic beads as disclosed herein in a manner that renders them resistant to interaction with enzymes such as RNase. Thus, the bio-complex of a single-strand nucleic acid such as RNA and the carbon coated magnetic beads as disclosed herein can provide a stable long-term storage vector for fragile single-strand nucleic acids.

It is contemplated that the stable stored single-strand nucleic acid material can comprise 10-5000 g of nucleic acids per microliter and 50-500,000 ng of carbon coated material per microliter, wherein the carbon coated material is preferably magnetic or silica nanoparticulate for this embodiment. The suspension for storage contains between 20% and 80% alcohols. The single-strand nucleic acid, while on the surface of the carbon-based material such as graphene, cannot be cleaved by enzymes such as RNase and will not spontaneously degrade.

Aspects of the disclosed implementations also include a method for fabricating the carbon coated magnetic beads that can be employed in the method and process disclosed herein. One such fabrication method is discussed in U.S. Published Application No. 2015-0170807 to Hagedorn, K. and Malizia, H, the specification of which is incorporated by reference herein. The referenced patent discloses methods for preparing magnetic beads. The magnetic beads prepared in carbon containing organic solvents such as xylenes or toluene may create a carbon coating on the surface of the magnetic beads suitable for use in the disclosed methods.

EXAMPLE I

Figure 7:
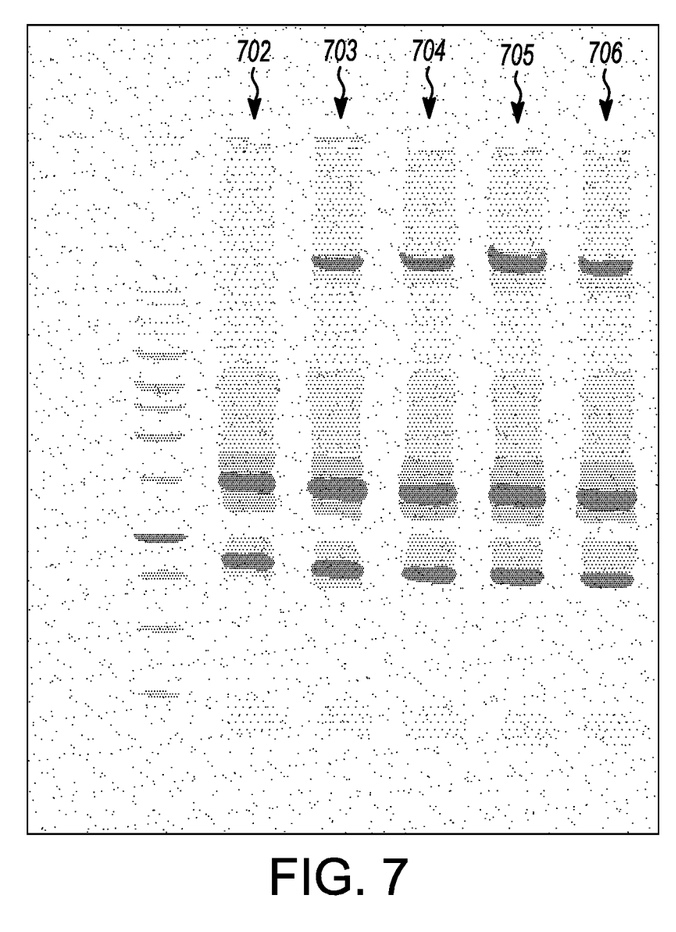
FIG. 7 is a gel electrophoresis image showing nucleic acids extracted from MCF7 immortalized breast cancer cells using 125 µl of: 2M, 3M, 4M, 5M, and 6M guanidinium thiocyanate with 500 µl of 70% ethanol and 30% pH 8 Tris.

To further illustrate the nucleic acid separation method described herein, the process was used to separate RNA from samples of 1 million MCF7 breast cancer cells with various process parameters and the RNA separated was quantified with gel electrophoresis in FIG. 7. Samples of 1 million MCF7 breast cancer cells were introduced into respective sterile glass containers at standard temperature and pressure. 125 μl of guanidinium thiocyanate solutions were added to each respective sample where the concentrations of guanidinium thiocyanate were 2M at reference 702, 3M at reference 703, 4M at reference 704, 5M at reference 705, and 6M at reference 706. The guanidinium thiocyanate solution also contained 1% Triton X-100, 10 mM EDTA, and 20 mM Tris, and the pH was adjusted to 6. Graphene coated magnetic beads as shown in FIG. 5 are then added to the respective samples. A solution of 70% ethanol is added to each sample to a constant 56% of the solution by volume, making the concentration of the guanidinium thiocyanate 0.4M at reference 702, 0.6M at reference 703, 0.8M at reference 704, 1M at reference 705, and 1.2M at reference 706 respectively. The graphene coated magnetic beads are 20 nm to 100,000 nm in size and have a carbon layer 1 angstrom to 50 nm thick. The carbon layers can be visualized in FIG. 5 as rings around the magnetic metal core. The magnetic metal core may be any material where Fe, Co, or Ni individually or combined compose more than 30% of material by atomic percent. The supernatant was separated from the carbon-coated magnetic beads complexed with nucleic acids and washed three times with a solution of 70% ethanol. 100 µl of purified water was then added and the single stranded nucleic acids were released into this water.

Portions of 10 µl of each respective sample was removed and subjected to electrophoresis. An agarose gel was cast and the samples were mixed with an ethenium bromide loading dye. The gel was run at 90V for 1 h.

This non-limiting example exemplifies how the process is industrially applicable by demonstrating RNA isolation from cells without DNA contamination. This non-limiting example also exemplifies the unexpected result that single stranded nucleic acids are extracted without contamination from double stranded nucleic acids when the concentration of chaotropic salts is between 0.1 M and 1M.

EXAMPLE II

Figure 8:
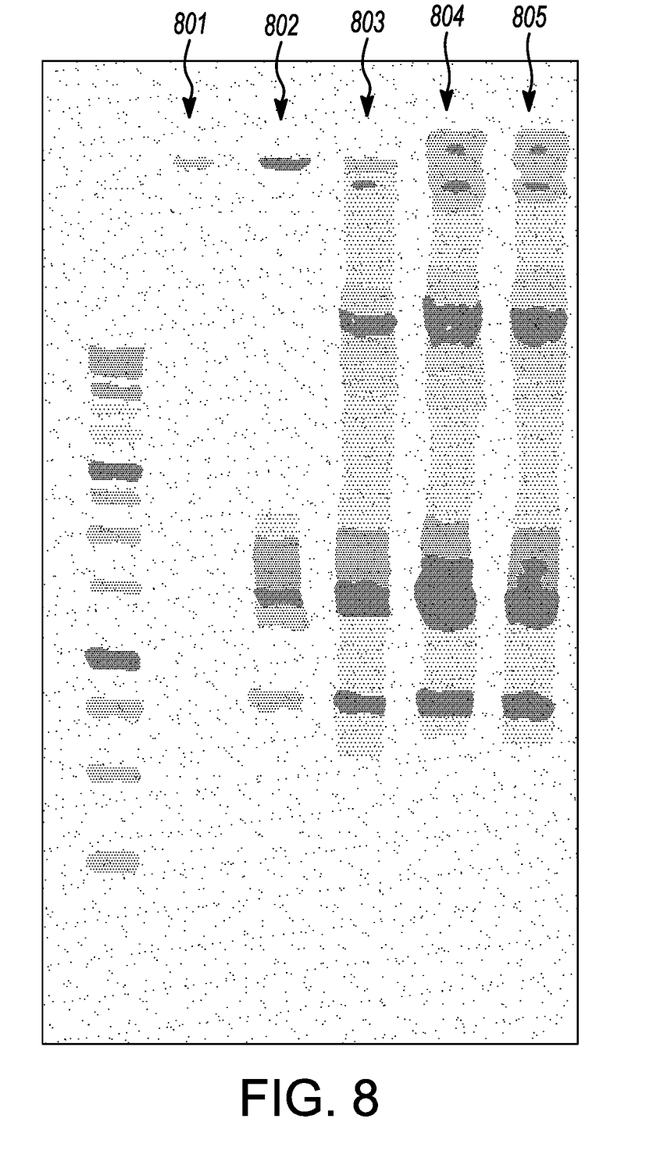
FIG. 8 is a gel electrophoresis image showing nucleic acids extracted from MCF7 immortalized breast cancer cells using 125 µl of 6M guanidinium thiocyanate without ethanol added and with 500 µl of 70% ethanol and 30% pH 8 Tris.

To further illustrate the nucleic acid separation method described herein, the process was used to separate RNA from samples of 1 million MCF7 breast cancer cells with various process parameters and the RNA separated was quantified with gel electrophoresis in FIG. 8. Samples of 1 million MCF7 breast cancer cells were introduced into respective sterile glass containers at standard temperature and pressure. 125 µl of 2M guanidinium thiocyanate solutions were added to each respective sample. A solution of 70% ethanol is added such that the concentration of ethanol is 0% at reference numeral 801, 31% by volume at reference numeral 802, 43% by volume at reference numeral 803, 49% by volume at reference numeral 804, and 56% by volume at reference numeral 805. It is observed that when 6M guanidinium thiocyanate solution is provided with carbon coated magnetic beads but without ethanol as previously described, single stranded nucleic acids are separated from the mixture but with poorer yield. The addition of ethanol has the unexpected result of enhancing recovery yield.

Portions of 10 µl of each respective sample was removed and subjected to electrophoresis. An agarose gel was cast and the samples were mixed with an ethidium bromide loading dye. The gel was run at 90V for 1 h.

This non-limiting example exemplifies how the process is industrially applicable by demonstrating RNA isolation from cells without DNA contamination. This non-limiting example also exemplifies the unexpected result that single stranded nucleic acids are extracted without contamination from double stranded nucleic acids when the concentration of alcohols is between 20% and 80% of the solution by volume.

EXAMPLE III

Figure 9:
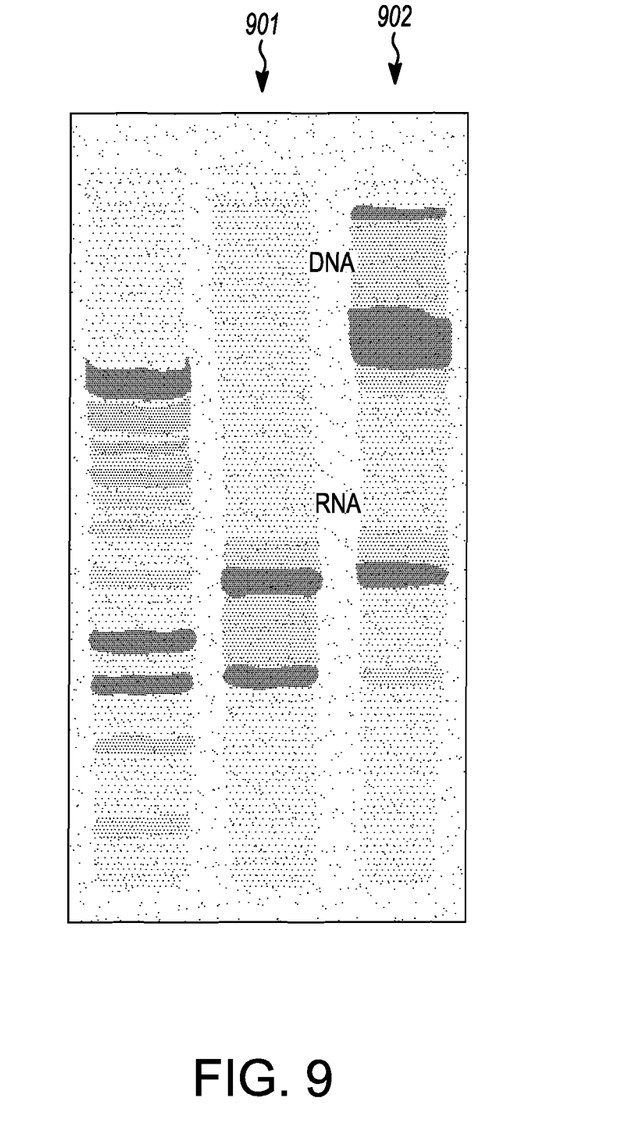
FIG. 9 is a gel electrophoresis image comparing nucleic acids extracted from MCF7 immortalized breast cancer cells using a buffer composed of 125 µl of 2M guanidinium thiocyanate and 500 µl of 70% ethanol and carbon coated magnetic beads compared with a nucleic acid isolation kit sold by Fisher Scientific.

FIG. 9 compares RNA extraction from 1 million MCF7 breast cancer cells using process outlined in Example I in the first lane 901 to the Thermo Fisher MirVana Total RNA Extraction Kit using the procedure described in that kit in the second lane at reference numeral 902. The Thermo Fisher MirVana Total Extraction Kit is a state-of-the-art kit from one of the largest life science suppliers in the world. The most noticeable difference is the absence of DNA contamination. DNA contamination is a problem for RNA analysis because PCR amplification cannot be performed with DNA contamination. Heretofore, the DNA contamination had to be removed with DNase, an enzyme which destroys DNA. This is both expensive and slow. The second noticeable difference is improved yield of small RNA, which is important for applications which analyze short RNA such as Micro RNA for diagnostic and research applications.

While the invention has been described in connection with certain embodiments, it is to be understood that the invention is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method for separating single stranded ribonucleic acid from associated biological material, the method comprising:
creating a complex of a three-dimensional carbon coated material and single stranded ribonucleic acid from a mixture containing single stranded ribonucleic acids, double stranded nucleic acids, the carbon coated material, at least one chaotropic salt and at least one alcohol having between one and four carbon atoms, wherein the at least one chaotropic salt present at a concentration from 0.01M to 3M, wherein the alcohols are present as 5 vol % to 99 vol %, and wherein the carbon coating present on the three-dimensional carbon coated material is selected from the group consisting of graphene, pyrolytic carbon and mixtures thereof; and
after the complex of the three-dimensional carbon coated material and single stranded ribonucleic acid has been created, removing the three-dimensional carbon coated material complexed with single-stranded ribonucleic acid from the mixture.

2. The method of claim 1, wherein chaotropic salt is a guanidinium salt composed of a guanidinium cation and an anion selected from the group consisting of chloride, bromide, fluoride, acetate, sulfate, nitrate, carbonate, thiocyanate and mixtures thereon.

3. The method of claim 1, wherein the chaotropic salt is present at a concentration between 0.01M and 0.6M.

4. The method of claim 1, wherein the alcohol is present in an amount between 10 vol % and 85 vol %.

5. A method for isolating nucleic acids having a defined sequence from an aqueous solution containing single stranded ribonucleic acid and double stranded nucleic acid after the aqueous solution has been contacted with at least one nucleic acid probe that is complementary with amino acids present on at least a portion of nucleic acid present in the aqueous solution, for an interval sufficient for the at least one nucleic acid probe to duplex with amino acid sequences present on at least a portion of the nucleic acid present in the aqueous solution to produce an admixture composed of duplexed nucleic acid material and non-duplexed nucleic acid material, the method comprising:
to the admixture containing duplexed nucleic acid material and non-duplexed single-stranded ribonucleic acid material, adding carbon-coated material, at least one chaotropic salt and short-chain alcohol, the short-chain alcohol present in an amount between 2 vol % and 99 vol %, the carbon coated material having a substrate having a core, the core having an outer surface, the carbon coated material further having an outer carbon coating overlying the outer surface of the core, the outer carbon coating having a thickness between 1 angstrom and 50 nm;

allowing contact for an interval sufficient to permit association between the carbon coated material and at least a portion of the single stranded ribonucleic acid material present in the admixture; and separating carbon-coated material complexed with the single stranded ribonucleic acid material from liquid supernatant, the liquid supernatant containing duplexed double stranded nucleic acid.

6. The method of claim 5, wherein the carbon coated material is configured as beads, wherein at least the core is magnetic and contains at least 30% by weight of a metal selected from the group consisting of Ni, Fe, Co, or mixtures thereof and wherein the carbon coating is selected from the group consisting of graphene, pyrolytic carbon and mixtures thereof.

7. The method of claim 5, wherein the chaotropic salt is added in an amount sufficient to provide a concentration between 0.01M and 3M.

8. The method of claim 7, wherein chaotropic salt is selected from the group consisting of a guanidinium salts, urea, thiourea, lithium acetate, lithium perchlorate, magnesium chloride and mixtures thereof.

9. The method of claim 8, wherein chaotropic salt is a guanidinium salt composed of a guanidinium cation and an anion selected from the group consisting of chloride, bromide, fluoride, acetate, sulfate, nitrate, carbonate, thiocyanate and mixtures thereof.

10. The method of claim 9, wherein the concentration of the chaotropic salt is between 0.01 and 8M.

11. The method of claim 5, wherein the short chain alcohol is selected from the group consisting of methanol, ethanol, propanol, isopropanol, phenol, and mixtures thereof.

12. The method of claim 5, wherein the separating step results in a complex of carbon-coated magnetic beads and nucleic acid, and the separating step includes subjecting the complex of carbon-coated magnetic beads and nucleic acid to at least one of a magnetic field, a centrifugal force, precipitation, competitive binding, or mixtures thereof.

13. The method of claim 5, wherein a concentration of the short-chain alcohol is between 10% and 95%.

14. The method of claim 1, wherein the carbon-coated material comprises a substrate composed of a particulate core having an outer surface and an outer carbon coating overlying the outer surface of the particulate core, the outer carbon coating having a thickness between 1 angstrom and 50 nm.

15. The method of claim 5, further comprising:

after separating the carbon-coated material from the liquid supernatant, releasing single stranded nucleic acid from attachment to the separated carbon-coated material, wherein the releasing step occurs with addition of water or suitable buffer solution into contact with the separated carbon-coated material.

16. The method of claim 15, wherein the removal step includes at least one of the following: centrifugation, precipitation, competitive binding, subjecting the water or suitable buffer solution in contact with the separated carbon coated material to a magnetic field.

17. The method of claim 5, wherein the carbon-coated material is configured as individual beads, each bead having an interior core and an outer surface, the beads composed of one of the following: a magnetic metal containing at 30% by weight of a metal selected from the group consisting of Ni, Fe, Co, or mixtures thereof, silica or polymeric substrates, and a carbon coating, wherein the carbon coating is present as a carbon layer on at least a portion of the outer surface of the individual beads, the carbon layer comprising at least one of graphene, pyrolytic carbon or a mixture of graphene and pyrolytic carbon, and wherein multivalent cations are associated with alkali earth metals or alkali earth metal salts or mixtures thereof.

18. The method of claim 5, wherein the at least one nucleic acid probe is a chain of nucleic acids selected such that the chain of nucleic acids contains complementary bases with corresponding positions to the single stranded nucleic acid that is to be isolated or purified.

19. The method of claim 5, wherein the at least one nucleic acid probe may be DNA or a synthetic nucleic acid and wherein the method further comprises the step of quantifying the sequence for study by performing PCR on the liquid supernatant that remains after removal of carbon coated magnetic material and associated single stranded nucleic acids.

* * * * *